US008128705B2

(12) United States Patent
Birkbeck et al.

(10) Patent No.: US 8,128,705 B2
(45) Date of Patent: Mar. 6, 2012

(54) ASSEMBLY FOR USE IN IMPLANTATION OF A JOINT COMPONENT

(75) Inventors: Alec Birkbeck, Leeds (GB); Dean Cowan, Leeds (GB)

(73) Assignee: DePuy International Limited (GB)

( * ) Notice: Subject to any disclaimer, the term of this patent is extended or adjusted under 35 U.S.C. 154(b) by 8 days.

(21) Appl. No.: 12/593,348

(22) PCT Filed: Mar. 27, 2008

(86) PCT No.: PCT/GB2008/001060
§ 371 (c)(1),
(2), (4) Date: Mar. 3, 2010

(87) PCT Pub. No.: WO2008/117058
PCT Pub. Date: Oct. 2, 2008

(65) Prior Publication Data
US 2010/0168865 A1    Jul. 1, 2010

(30) Foreign Application Priority Data
Mar. 28, 2007  (GB) .................................. 0705942.1

(51) Int. Cl.
*A61F 2/36* (2006.01)
(52) U.S. Cl. .................................... 623/23.11
(58) Field of Classification Search .... 623/19.11–19.14, 623/22.11, 22.15–22.18, 23.47–23.48, 23.43–23.45
See application file for complete search history.

(56) References Cited

U.S. PATENT DOCUMENTS
5,362,311 A    11/1994  Amino
2002/0016634 A1    2/2002  Maroney
2003/0028253 A1 *    2/2003  Stone et al. ................ 623/19.14
2004/0226343 A1    11/2004  Babler

FOREIGN PATENT DOCUMENTS

| EP | 498518 A1 | 8/1992 |
|---|---|---|
| EP | 931522 A1 | 7/1999 |
| EP | 1402856 A1 | 3/2004 |
| JP | 52028167 A | 3/1977 |
| WO | WO 0182843 A2 | 11/2001 |
| WO | WO 0182843 A3 | 2/2002 |
| WO | WO 2007125125 A1 | 11/2007 |

OTHER PUBLICATIONS

Sumitomo Chemical; English Abstract of JP Patent No. JP52028167A; Mar. 2, 1977; MicroPatent Report; 2009 MicroPatent LLC.

(Continued)

*Primary Examiner* — David Isabella
*Assistant Examiner* — Brian Dukert

(57) ABSTRACT

An assembly for use in a procedure for implantation of an orthopedic joint component, comprises a head part of the joint component which has a tapered bore within it, and a connector part which is tapered inwardly along its length so that it can be received snugly in the tapered bore in the head part, the connector part having a bore within it. A tool includes a spigot which fits snugly into the bore in the connector part. Each of the tool and the connector part has a face which contact one another when the spigot on the tool is fully received in the bore in the connector part, and in which each of the said faces extends generally transverse relative to the aligned axes of the spigot and the bore.

19 Claims, 7 Drawing Sheets

OTHER PUBLICATIONS

Metasul® LDH® Large Diameter Head with Durom® Acetabular Component Surgical Technique; Product Brochure; 97-1081-002-00 Rev. 1 ©2007, 2008 Zimmer, Inc.; www.zimmer.com.

PCT International Search Report PCT/GB2008/001060 dated Jul. 14, 2008.

UK Search Report GB0705942.1 dated Jul. 5, 2007.

* cited by examiner

FIG. 1
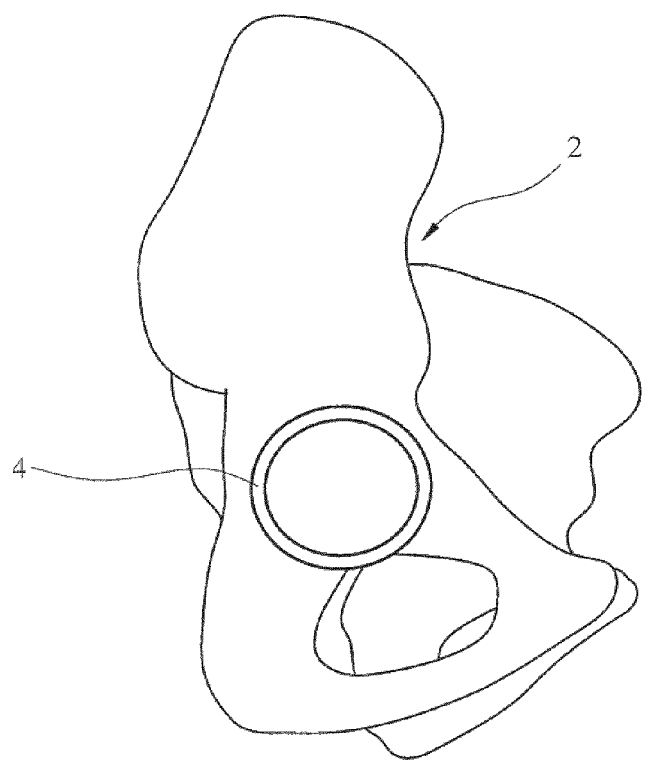
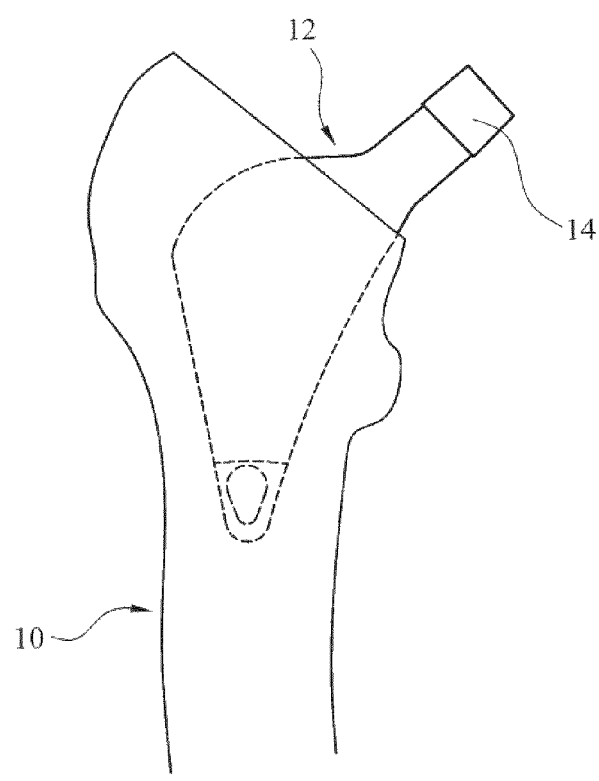
FIG. 2

ASSEMBLY FOR USE IN IMPLANTATION OF A JOINT COMPONENT

CROSS REFERENCE TO RELATED APPLICATION

The present application is a continuation of International Patent Application PCT/GB2008/001060 filed Mar. 27, 2008.

BACKGROUND OF THE INVENTION

This invention relates to an assembly for use in a procedure for implantation of an orthopaedic joint component.

US-A-2005/0197708 discloses a humeral component of a shoulder joint prosthesis which comprises a stem part, a head part, and a connector part which can be fitted into a bore in the head part, and has a bore formed in it to receive a spigot on the stem part. The eccentric arrangement of the bore in the head part relative to the axis of the head part, and the eccentric arrangement of the bore in the connector part eccentric relative to the axis of the connector part, allow the distance through which the head part is offset relative to the stem part, and the orientation of that offset, to be adjusted to suit the requirements of a patient. This can facilitate variation of effective arm length, and the extent of retroversion and anteversion.

It is important when assembling parts of a modular joint prosthesis component such as that disclosed in US-A-2005/0197708 to ensure that the parts are assembled securely, so that there is no possibility of relative movement between the parts.

The present invention provides an assembly for preparing a joint prosthesis component for implantation, which includes a tool on which the component can be placed, and which facilitates the application of an assembly force to the component.

Accordingly, in one aspect, the invention provides an assembly for use in a procedure for implantation of an orthopaedic joint component, which comprises:
 a. a head part of the joint component which has a tapered bore within it,
 b. a connector part which is tapered inwardly along its length so that it can be received snugly in the tapered bore in the head part, the connector part having a bore within it, and
 c. an assembly tool which includes a spigot which fits snugly into the bore in the connector part,
  in which each of the tool and the connector part has a face which contact one another when the spigot on the tool is fully received in the bore in the connector part, and in which each of the said faces extends generally transverse relative to the aligned axes of the spigot and the bore.

In another aspect, the invention provides a method of assembling an orthopaedic joint component prior to implantation, which comprises:
 a. providing a head part of the joint component and a connector part, in which the head part has a tapered bore within it in which the connector part can be received in a snug fit, and in which the connector part has a bore within it,
 b. fitting the connector part into the bore in the head part,
 c. placing the connector part on a tool which contacts a surface of the connector part which faces away from the head part, the tool having a spigot which is received in the bore in the connector part when the connector part is placed on the tool, and
 d. applying force to the head part in a direction towards the connector part.

BRIEF SUMMARY OF THE INVENTION

The present invention facilitates the application of an assembly force to a modular joint prosthesis component. The tool can help to hold the component against movement during the application of the assembly force. The tool can help to orientate the component, to facilitate control of the direction in which an assembly force is applied to the component. The contacting transverse faces of the tool and the connector part can help to ensure that the assembly force is transmitted from the head part to the connector part, without the connector part becoming fastened to the tool. Release of the connector part from the tool can be facilitated by provision of a quantity of a compressible material on the tool spigot, as discussed below.

The tool preferably includes a base, and the spigot extends upwardly from the base. Preferably, mass of the tool is at least about 300 g, more preferably at least about 500 g, especially at least about 1250 g. Preferably, the tool is made at least partially from a metal. Suitable metals are known for use in the manufacture of surgical instruments. Examples of suitable metals include certain stainless steels.

The base of the tool can be rounded, for example circular. The base can be without openings extending through it. However, it can be preferred that there are openings extending through the base. In particular, it can be preferred that there is at least one opening extending through the base to permit inspection of the joint component when it is positioned on the spigot. For example, it can be appropriate for the base to comprise a plurality of spokes extending outwardly from a central spigot. For example, there might be three or four or five or six or more spokes. It can be preferred for the base to include a rim which extends between at least some of the spokes around the periphery of the base.

It can be preferred for the base to have openings in it when the step of positioning the connector part on the tool is carried out before the step of locating the bore in the head part over the connector part. The provision of openings can facilitate inspection of the parts of the joint component to ensure appropriate alignment of the head part relative to the connector part.

Preferably, the face of the tool which contacts the connector part when the spigot is fully received in the bore is a surface which extends around the base of the spigot. This has the advantage of providing the possibility for the connector around its entire periphery.

The face of the tool which contacts the connector part when the spigot is fully received in the bore can contact the connector part at spaced apart points around its periphery. For example, when the base of the tool comprises a plurality of spokes, the connector part can contact the base on each of the spokes. It will often be preferred however that the tool contacts the connector part continuously around its periphery. When the tool has a plurality of spokes, it can be preferred that the spokes extend from a point radially outside the face which contacts the connector part.

It is particularly preferred that the face of the connector part which contacts the tool when the spigot is fully received in the bore is a surface which extends around the bore opening. The face will generally be directed away from the head part of the assembly along the axis of the bore in the connector part. The surface area of the face of the connector part where it contacts the tool should be sufficient to ensure that the connector part is not deformed when an assembly force is applied to the joint component parts on the tool.

The shape and geometry of the tool should be such that, when the connector part is fully seated on the tool spigot so that the facing surfaces of the tool and the connector part are in contact, the head part is not in direct contact with the tool.

Preferably, the angle between the axis of the spigot and the plane of the said face on the tool is between about 75° and about 105°, more preferably between about 85° and about 95°. It is particularly preferred that the angle between the axis of the spigot and the plane of the said face on the tool is about 90°.

Preferably, the angle between the axis of the bore in the connector part and the plane of the said face on the connector part is between about 75° and about 105°, more preferably between about 85° and about 95°. It is particularly preferred that the angle between the axis of the bore in the connector part and the plane of the said face on the connector part is about 90°.

Preferably, the angle between the plane of the said face on the connector part and the plane of the said face on the tool is not more than about 15°, more preferably not more than about 5°. It is particularly preferred that the plane of the said face on the connector part is approximately parallel to the plane of the said face on the tool.

It can be preferred for the bore in the connector part to be inwardly tapered. This can facilitate connection of the connector part to another part of the joint prosthesis component. For example, the joint prosthesis component might comprise a stem part in addition to the head and connector parts referred to above. The stem part might have a tapered spigot which can be received bore in the connector part. When the bore in the connector part is inwardly tapered, it can be preferred that the spigot on the tool is similarly tapered.

Preferably, the assembly includes a layer of a resilient material which covers at least part of the surface of the spigot, so that it is compressed between the surface of the spigot and the internal surface of the bore in the connector part when the spigot is received in the bore. The resilient material should be softer than the material of the internal surface of the bore in the connector part so that the internal surface of the bore is not damaged on contact with the tool. The resilient material on the spigot can help to stabilise the connector part on the tool. The deformability of the material on the spigot means that the connector part can be seated on the spigot until the transverse faces on the tool and the connector part are in contact with one another.

Preferably, the resilient material extends around the spigot in an annular arrangement. For example, the spigot can have an annular groove formed in it and the resilient material is provided as an O-ring which is located partially in the groove. It can be particularly preferred for some applications for the spigot to have at least two O-rings on it, in spaced apart locations along its length.

Suitable materials for provision on the tool spigot, for compression between the surface of the spigot and the internal surface of the bore, include certain elastomers such as natural and synthetic rubbers, especially silicone rubbers, rubbers based on ethylene-propylene copolymers and so on.

Preferably, the assembly includes at least one pad of a non-slip material on the surface of the tool which faces away from the spigot, and from the connector part when the tool is in use. The non-slip material should have a higher coefficient of friction relative to hard surfaces such as are found in operating theatres, such as surfaces of stainless steel, thermo-setting polymers and the like, compared with the material of the remainder of that surface of the tool, which might be a metal such as a stainless steel. Examples of suitable non-slip materials include certain elastomers such as certain natural and synthetic rubbers. When the base of the tool has a rim which extends at least partially around the base (including such tools in which the base does not have any openings in it), it can be preferred for the pad of non-slip material to be provided the form of a ring which extends around at least part of the periphery of the tool, preferably continuously around the entire periphery of the base. The provision of the non-slip material in this way finds particular application when the tool is placed on a surface with the joint component parts on the tool, so that the tool functions as a stand during the assembly of the components. However, the tool can be used in a reverse sense, where the tool is fitted to an upwardly facing surface of the components while they are being assembled. An impaction force can then be applied to the assembly through the tool.

The assembly of the invention can be used in the assembly of joint prosthesis components which include the humeral component of a shoulder joint prosthesis and the femoral component of a hip joint prosthesis. The assembly of the invention finds particular application in relation to a hip joint prosthesis, where the high loads which are applied to the prosthesis after implantation make proper and secure assembly of the parts of a modular component particularly important.

Preferably, the bearing surface of the head part is part-spherical with an approximately constant radius. Preferably, the radius of the sphere which defines the bearing surface is at least about 7 mm, more preferably at least about 9 mm, for example at least about 11 mm. Preferably, the radius is not more than about 20 mm, more preferably not more than about 15 mm, for example not more than about 12 mm.

Preferably, the angle of arc through which the bearing surface of the head part extends is at least about 180°, more preferably at least about 190°, for example at least about 200°.

Preferably, the axis of the head part defined by its bearing surface and the axis of the bore in the head part are approximately parallel. The distance between the axis of the head part defined by its bearing surface and the axis of the bore in the head part can be at least about 2 mm, for example at least about 4 mm. The distance between the axis of the head part defined by its bearing surface and the axis of the bore in the head part can be not more than about 10 mm, for example not more than about 8 mm, or not more than about 6 mm or not more than about 4 mm.

Preferably, the axis of the connector part defined by its external surface and the axis of the bore in the connector part are approximately parallel. The distance between the axis of the connector part defined by its external surface and the axis of the bore in the connector part can be at least about 2 mm, for example at least about 4 mm. The distance between the axis of the connector part defined by its external surface and the axis of the bore in the connector part can be not more than about 10 mm, for example not more than about 8 mm, or not more than about 6 mm or not more than about 4 mm.

Preferably, the diameter of the bore in the head part at the widest point at which it is contacted by the external surface of the connector part when assembled is not more than about 35 mm, more preferably not more than about 30 mm. Preferably, the diameter of the bore in the head part at the widest point at which it is contacted by the external surface of the connector part when assembled is at least about 10 mm, more preferably at least about 15 mm, for example at least about 20 mm.

For some applications, the connector part can have at least two inwardly tapered bores formed within it, each having a circular cross section, and each capable of receiving a spigot on the stem part in a snug fit, in which the axes of the bores are approximately and the distance from the axis of the connector part defined by its external surface to the axis of one of the bores is different from the distance from the axis of the connector part defined by its external surface to the axis of another of the bores. Selection of the bore in the connector part in which the spigot is inserted can be used to select the configuration of the assembled femoral component to suit the requirements of a patient.

It will generally be preferred for the stem part or the connector part or both to be formed from a metal. Suitable metals for use in the manufacture of one or each these parts include certain stainless steels, titanium and its alloys, and alloys which include cobalt and molybdenum.

It will generally be preferred for the head part of the component to be formed from one or more of a metal and a ceramic material. Suitable metals for use in the manufacture of one or each these parts include certain stainless steels, titanium and its alloys, and alloys which include cobalt and molybdenum. Suitable ceramic materials include certain oxides, nitrides and carbides of elements such as aluminium, zirconium, titanium and so on.

The bore in the head part, and optionally also the bore in the connector part, and the external surface of the connector part, should be tapered so that there is an interference fit between the mating surfaces when the parts are assembled. As is known, for many combinations of materials, appropriate locking an be achieved when the angle between the surface and the axis of the part in question is in the region of, for example, from about 2.5° to about 5°.

BRIEF DESCRIPTION OF THE DRAWINGS

Embodiments of the invention will now be described by way of example with reference to the accompanying drawings, in which:

FIG. 1 is a view of a prepared acetabulum, in which an acetabular cup component has been implanted.

FIG. 2 is a view along the anterior posterior axis of the head of a femur, in which a stem part of a femoral component of a hip joint prosthesis has been implanted.

DETAILED DESCRIPTION OF THE INVENTION

Figure 3:
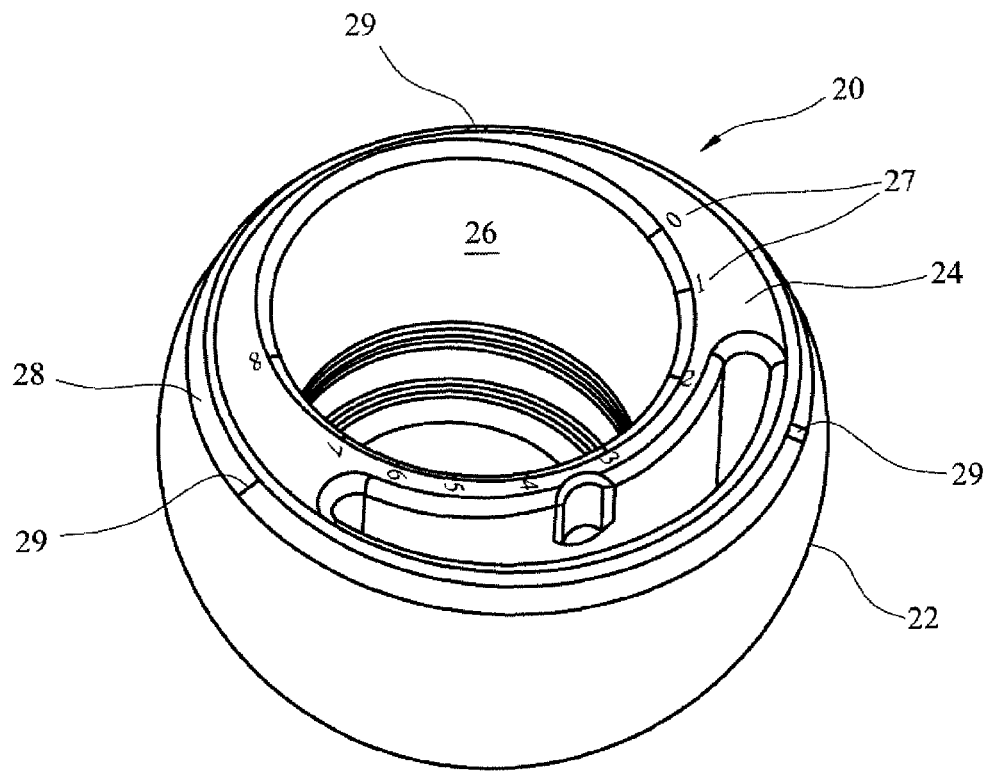
FIG. 3 is a view from below of a head part of a femoral component.

Referring to the drawings, FIG. 1 shows a pelvis 2 which is been reamed to receive the acetabular cup component 4 of a hip joint prosthesis. The acetabular cup component has been implanted using conventional techniques.

FIG. 2 shows the head portion of a femur 10 which has been resected at the base of the femoral neck. The intramedullary cavity has been prepared using conventional techniques (by reaming or broaching or a combination of the two) to receive the stem part 12 of the femoral component of a hip joint prosthesis. The stem part can be fastened in the femur by means of a bone cement material, as is known. The stem part can be fastened in the femur without the use of a bone cement material, as is known.

The stem part has a tapered spigot 14 at its exposed end on which the head part of the femoral component can be fitted. The dimensions of the spigot on the stem part are in line with existing stem parts of femoral components of hip joint prostheses.

FIG. 3 shows the head part 20 of a femoral component of a hip joint prosthesis according to the present invention. The head part has a spherical bearing surface 22 and an opposite reverse face 24. The spherical bearing surface extends through an angle of arc of about 200°. The radius of the bearing surface is 18 mm. The distance from the reverse face of the head part to the point where the polar axis intersects the bearing surface is from 28.25 to 41.8 mm.

A tapered bore 26 is formed in the reverse face 24. The bore has a circular cross-section. At the reverse face, the diameter of the bore is from 24.2 to 28.6 mm. The depth of the bore, measured from the reverse face of the head part to the blind end of the bore, is from 9.0 to 11.5 mm. The angle between the wall of the bore and its axis (which is half of the angle defined by the diametrically opposite walls of the bore) is 5°.

The bore 26 is offset relative to the polar axis (which is the axis extending through the centre of the sphere defined by the bearing surface, perpendicular to the reverse face). The distance between the axis of the bore and the polar axis is from 2 to 4 mm.

The head part has a series of markings 27 on its reverse face. These relate to the distance through which the head part is offset relative to the axis of the stem part when the femoral component is assembled, as discussed below.

The head component has a chamfer surface 28 extending around its periphery where the chamfer and reverse faces come together. The chamfer surface is planar when the component is viewed in cross-section. The angle between the chamfer surface and the polar axis is about 50°. The chamfer surface has three markings 29 at spaced apart points. The markings are distinguishable from one another.

Figure 4:
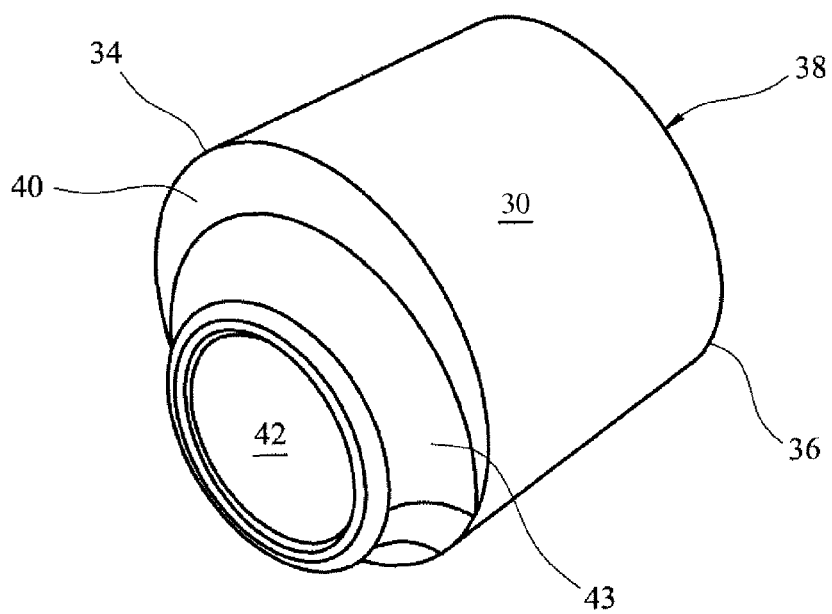
FIG. 4 is an isometric view from below of a connector in place which can be used to connect the head part shown in FIG. 3 to the stem part shown in FIG. 2.

FIG. 4 shows a connector 30 which can be used to connect the head part to the stem part 12 of the femoral component. The connector is circular when viewed from above and is tapered inwardly along the axis defined by its external surface 32. The diameter of the connector at its widest 34 point is from 24.2 to 28.3 mm. The diameter of the connector at its narrowest point 36 is from 22.45 to 20.7 mm. The depth of the connector measured from its top face 38 to its opposite bottom face 40 (not including the skirt which depends from the bottom face) is from 19.75 to 22.25 mm. The angle between the wall of the connector and its axis (which is half of the angle defined by the diametrically opposite walls of the connector) is 5°. The connector is therefore a snug fit in the bore 26 in the head part, with the top face 38 located within the bore 26 in the head part, and the bottom face 40 located adjacent to the reverse face 24 of the head part. When the connector is fully received in the bore 26 in the head part, the length of the contacting surfaces of the connector and the bore, measured along the axis of the bore, is from 19.75 to 22.25 mm. The widest point at which the connector is in contact with the bore is at the widest part of the connector part (that is at the bottom face 40). Accordingly, the ratio of the length of the contacting surfaces of the bore in the head part and the connector part when assembled, measured along the axis of the bore in the head part, to the diameter of the bore in the head part at the widest point at which it contacts the external surface of the connector part, is 1.23 (24.2:19.75) or 1.27 (28.3:22.25) in the two embodiments which are discussed.

The connector 30 has a bore 42 within it extending from the bottom face 40. The bore is tapered inwardly in a direction away from the bottom face of the connector. The bore is open at its opposite narrow end. The bore can be blind at its narrow end. A skirt 43 surrounds the bore at its open end on the bottom face 40.

The bore 42 in the connector is sized so that the spigot 14 on the stem is a snug fit within it.

Figure 5:
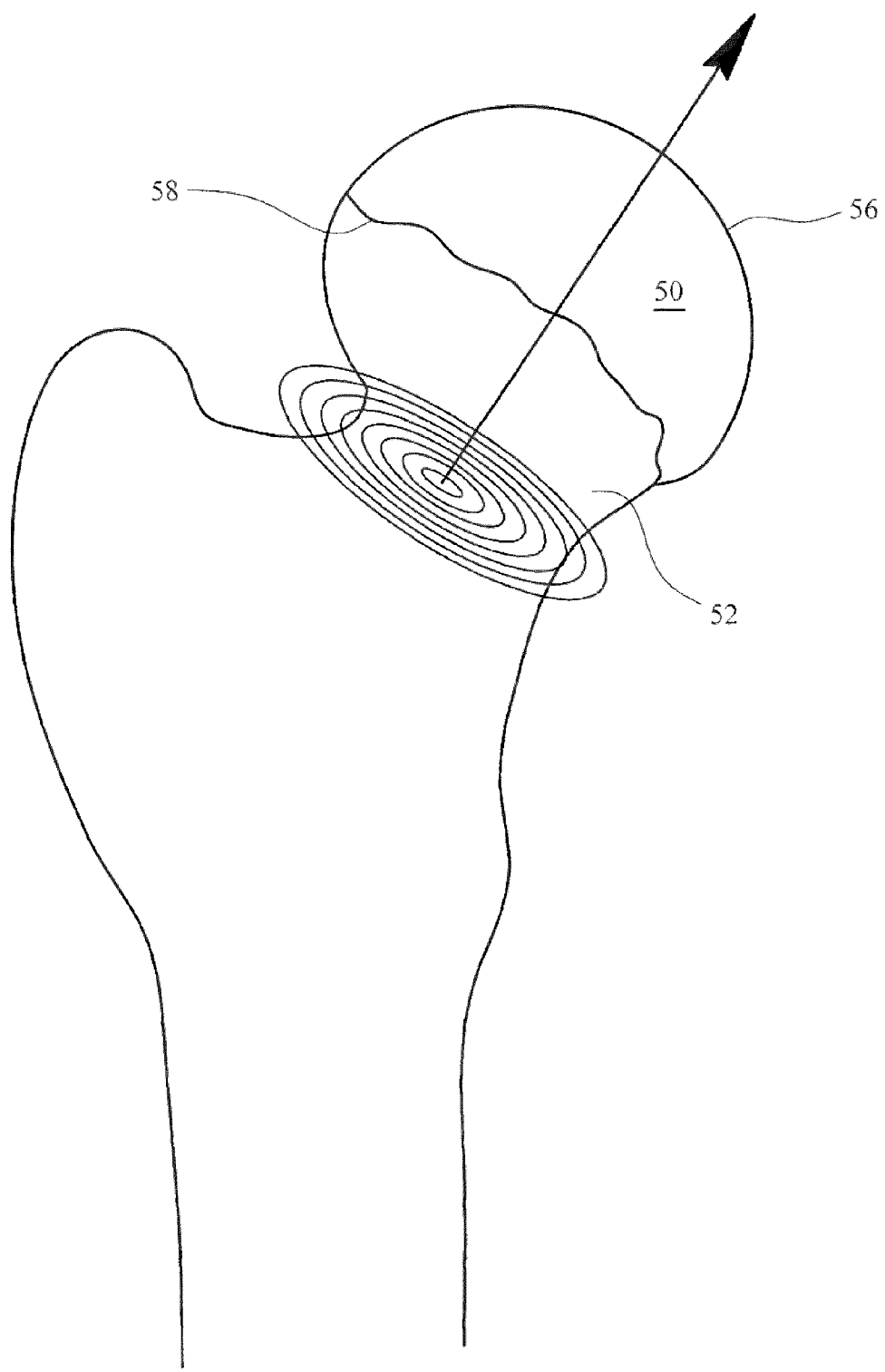
FIG. 5 is a view of the head of a femur to illustrate the offset of the bearing surface of the femoral head relative to the femoral neck.

FIG. 5 shows the head portion of a femur prior to any resection step in a procedure for replacement of a hip joint. The femur has a head part 50 and a neck 52 which extends between the head part and the femoral shaft 54. The outer bearing surface 56 of the head part is smooth, for articulation with a corresponding bearing surface within the acetabulum, and extends over the head part towards the femoral shaft to a boundary line 58. The bearing surface of the head part is defined by part of a sphere. The axis of the head part passes through the centre of the sphere, in a direction which is perpendicular to the plane which is defined by the boundary line 58.

The femoral neck 52 defines an axis which extends along its central core, between the femoral shaft and the head part.

The head part 50 of the femur can be offset relative to the femoral neck. A translational offset arises when there is a gap between the axis of the head part and the axis of the femoral neck. The size of the gap between the axes can be different from one patient to another, for example in the range 0 to 10 mm. The direction in which the axes are offset can vary, around the axis of the femoral neck.

Figure 6:
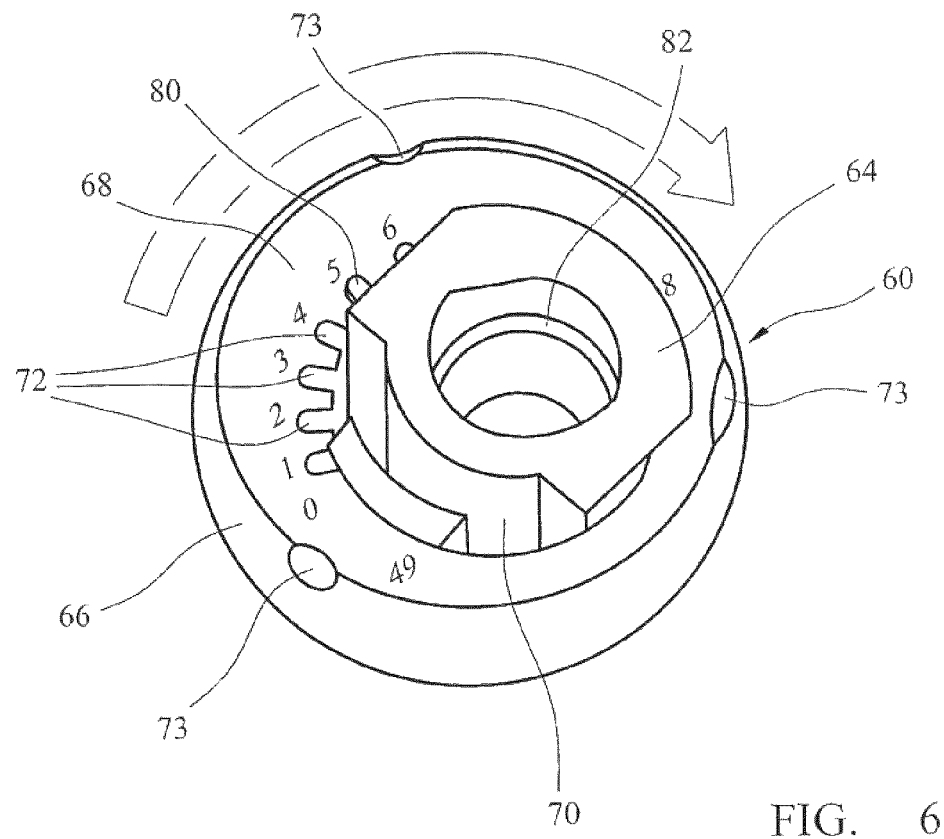
FIG. 6 is a view from below of a trial instrument which can be used to select the appropriate offset in an assembled femoral component.
Figure 7:
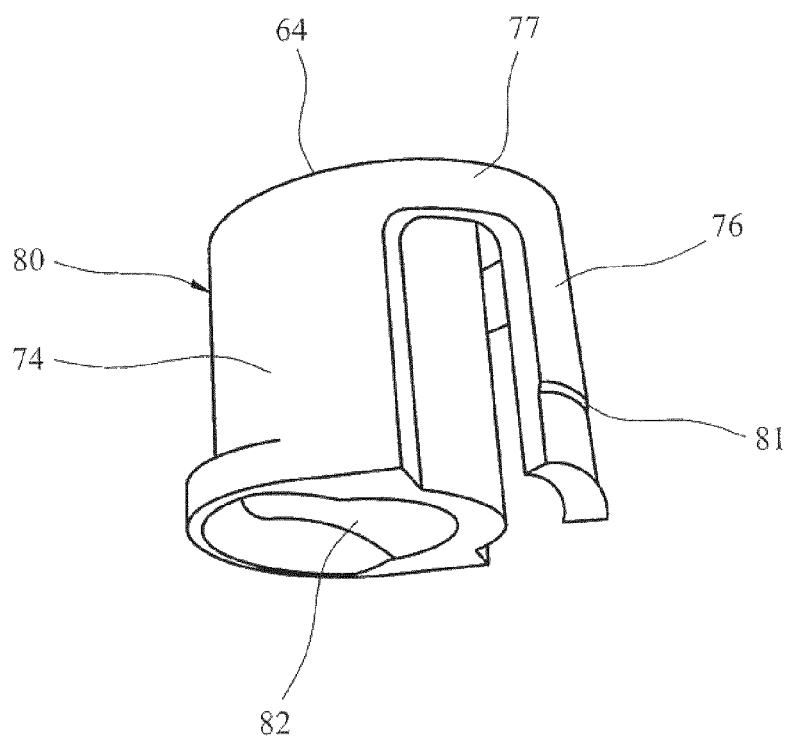
FIG. 7 is a side view of the trigger part of the trial instrument which is shown in FIG. 6.
Figure 8:
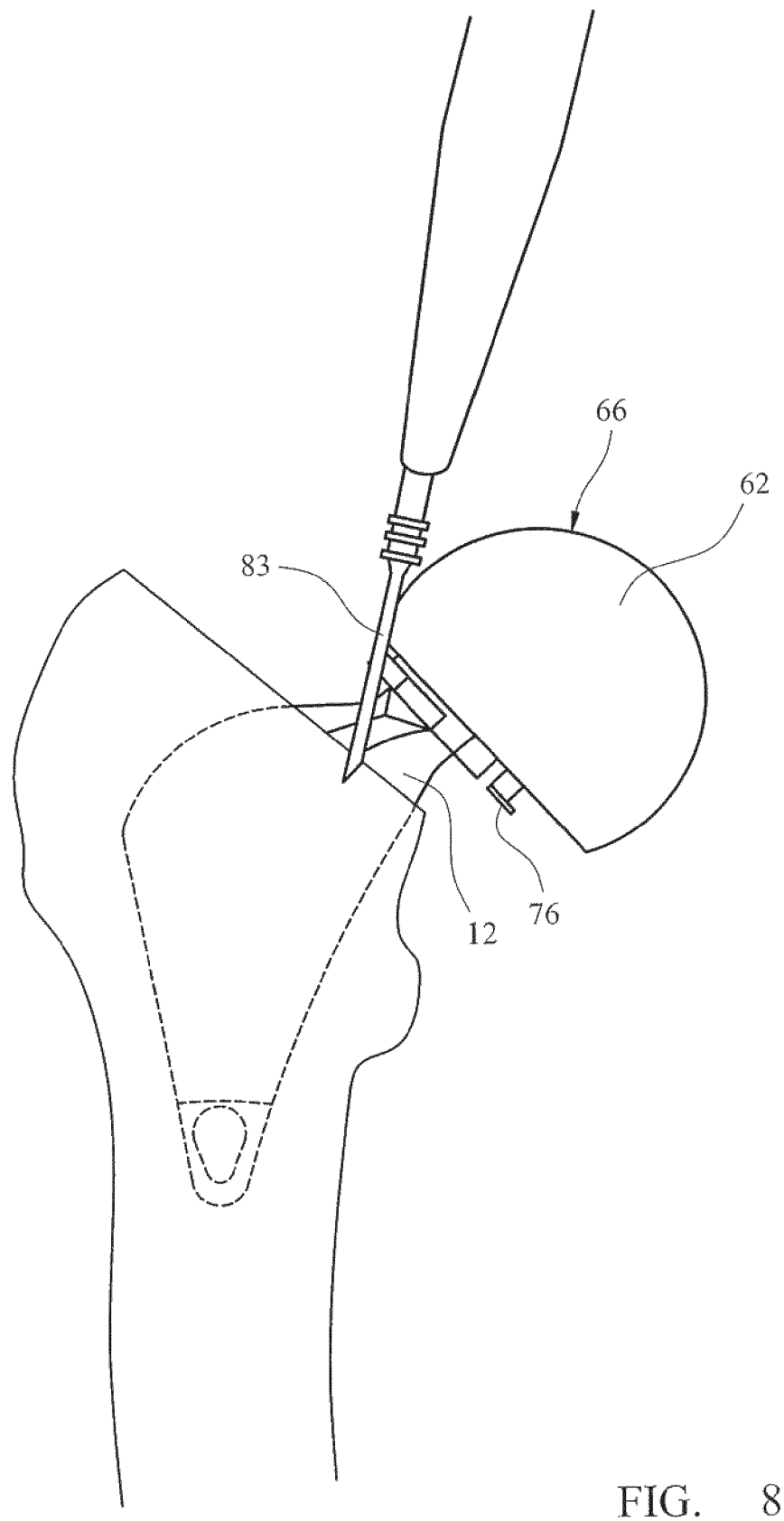
FIG. 8 is a side view of the head of the femur, with the trial instrument shown in FIG. 6 mounted on the stem part.

FIG. 6 shows an instrument 60 which can be used to trial the head part (with its connector) on an implanted stem part. The instrument comprises a trial head part 62 and a trial connector 64. The trial connector is shown in FIG. 7. The trial head part has a spherical outer surface 66 which corresponds to the bearing surface of the head part of the ultimate implant, and an opposite reverse face 68. The head part has a recess 70 within it extending inwardly from the reverse face towards the bearing surface. The recess is generally round when The recess has a plurality of grooves 72 in its side wall extending parallel to the axis of the recess. The trial head part can be formed from a metal such as a stainless steel or from a polymeric material.

The spherical outer surface 66 of the trial head part has three notches 73 at spaced apart points. The notches are distinguishable from one another, for example by means of distinguishing markings located adjacent to the notches.

The trial connector 64 is formed from a polymeric material. It comprises a body part 74 and a trigger 76 which is connected to the body part at one end 77. The material of the trigger 76, and of the body part when the trial connector is formed as a single piece) is sufficiently resilient that the trigger can be deformed inwardly towards the body part.

The body part has a rib 80 which is dimensioned so that it can fit into one of the grooves 72 in the side wall of the recess.

The trial head part and the trial connector have locking features so that the connector is retained within the recess 70 in the head part when the trigger is released, and can be removed from within the recess when the trigger is deformed towards the body part. The locking features can comprise an annular groove which extends around the recess, and a rib 81 on one or each of the body part and the trigger of the trial connector. When the rib is received in the groove, the trial connector is locked against removal from the bore in the trial head part. When the trigger 76 is squeezed towards the body part 74, the trial connector is able to move transversely within the recess in the body part so that the rib can be withdrawn from the groove, allowing the trial connector to be withdrawn from within the recess.

The body part 74 of the trial connector has a bore 82 formed in it. The bore is tapered inwardly in a direction away from the bottom face of the connector. The bore is open at its opposite narrow end. The bore is blind at its narrow end. The bore 82 in the trial connector is sized so that the spigot 14 on the stem is a snug fit within it.

Figure 9:
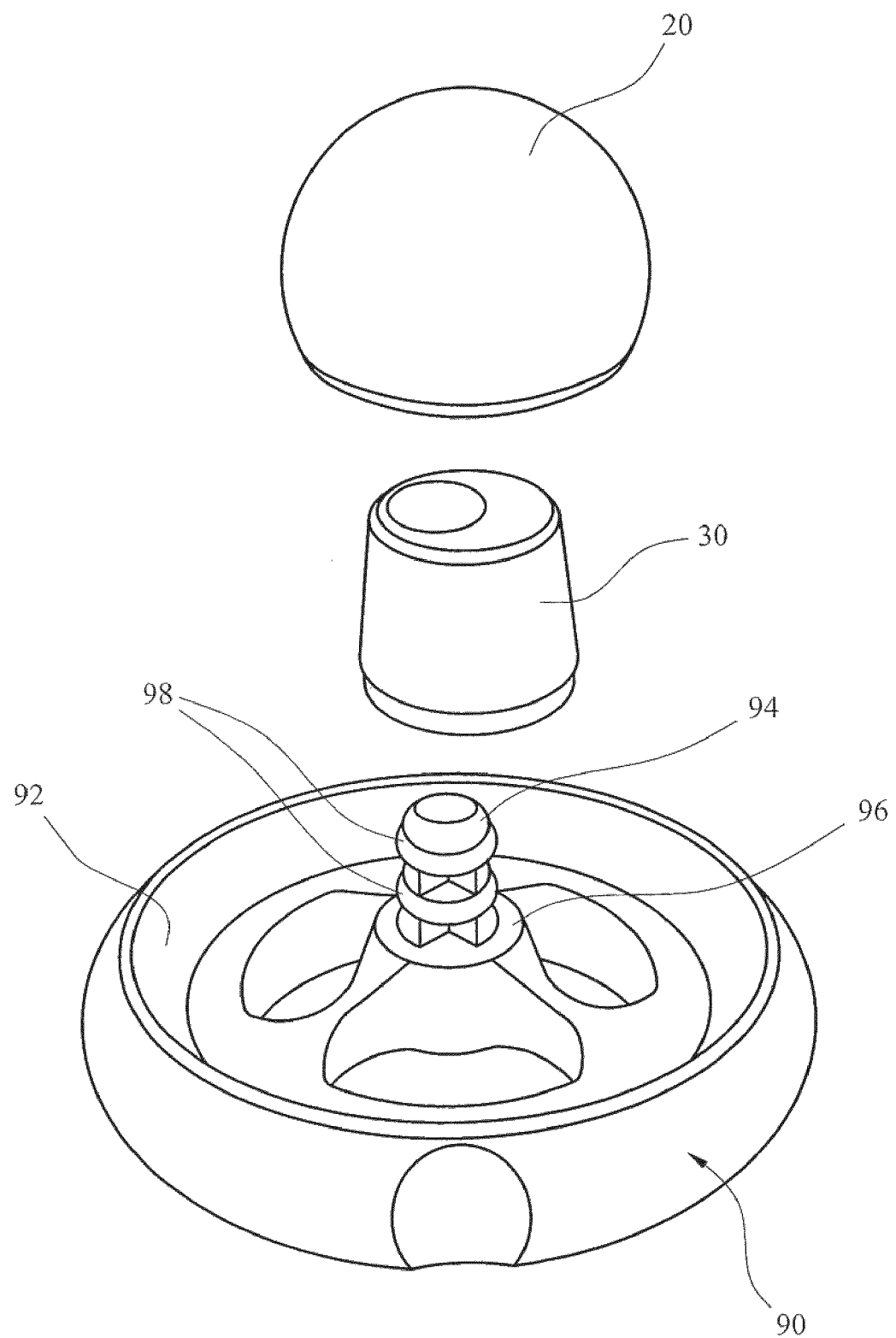
FIG. 9 is a side view of a tool which can be used to assemble the head part and the connector, shown in FIGS. 3 and 4 respectively.

FIG. 9 shows an assembly tool 90 which can be used in the assembly of the head part 20 of the femoral component and the connector 30. The tool comprises a base 92 having an upstanding spigot 94. The spigot has a collar 96 around it, which presents an upwardly facing surface. A pair of compressible O-rings 98 are provided on the spigot, located in annular grooves therein. The sizes of the spigot and the O-rings are such that the O-rings are compressed on contact with the internal wall of the bore 42 in the connector 30 when the connector is seated on the tool with the bottom face of the skirt 43 in contact with the collar 96 on the tool. This can help to retain the connector on the spigot, by virtue of the friction forces between the O-rings and the internal surface of the bore in the connector.

The assembly tool 90 is made from stainless steel. It can have a ring of a rubber material located in a groove in its lower face such that it protrudes from the groove to engage the surface on which the tool is placed when in use.

Figure 10:
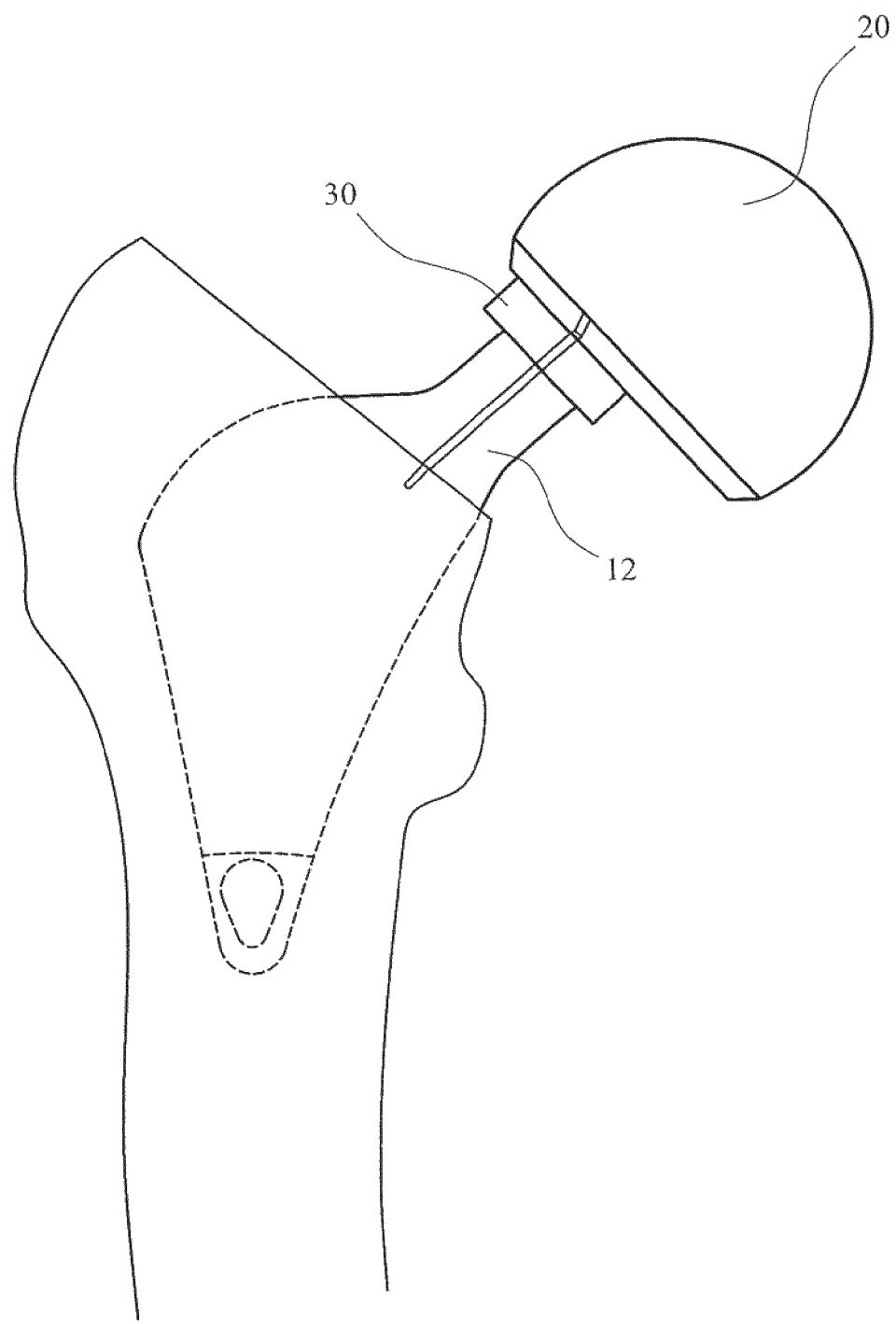
FIG. 10 is a view from one side of an assembled femoral component of a hip joint prosthesis according to the present invention.

FIG. 10 shows the femoral component of a hip joint prosthesis according to the present invention which has been assembled. The assembled femoral component comprises the head part 20, with the connector 30 located in the bore 26 therein. The spigot 14 on the stem part 12 of the femoral component is located in the bore 42 in the connector.

A procedure in which the invention can be implemented to provide a femoral component of a hip joint prosthesis can include the following steps.

Initial steps involve preparing the femur to receive the stem part. These steps are conventional, and include resection of the neck and head of the femur, and working on the intramedullary cavity in the femoral shaft so that it is appropriately dimensioned to receive the stem part.

Preparatory work on the patient might provide information as to the desired offset of the femoral head. The trial components described above with reference to FIGS. 4 to 6 can allow offsets to be assessed. Variations in the size of the gap between the axis of the head part and the axis of the femoral neck can be replicated by changing the angular relationship between the trial head part 62 and the trial connector 64, using the trigger to release the trial connector for movement in the recess in the trial head part. Variations in the direction in which the axes are offset can vary, around the axis of the femoral neck, can be replicated by rotating the trial components around the spigot 14 on the stem part 12.

Markings on the reverse face 68 of the trial head part 62 provide an indication of the size of the offset, which is then to be incorporated in the assembled head component.

A record of the angular orientation of the trial head part about the spigot 14 is made with reference to a selected one of the notches 73 on the spherical outer surface 66 of the trial head part, using a diathermy 83 to make a mark on bone tissue 84 immediately below the selected notch.

The size of the offset that is determined using the trial head part and the trial connector are reproduced in the head component with reference to the markings 28 on the reverse face 24 of the head part 20 (which are the counterparts to the grooves 72 in the side wall of the recess 70 in the reverse face 68 of the trial head part 62), and to a marking on the connector 30 (which is the counterpart to the rib 80 on the trial connector 64). The head part 20 and the connector 40 of the implant are assembled accordingly, and placed on the spigot 94 of the assembly tool 90. An impaction force is applied to the head part through an appropriate protector (such as a block of polyethylene which is configured to be a conforming fit on the bearing surface 22 of the head part 20). Application of the impaction force causes the connector to be forced downwardly on to the spigot 94 until the skirt 43 on the bottom face of the connector contacts the collar 96 on the tool, compressing the O-rings 98 on the spigot as necessary. When the skirt on the connector contacts the collar on the tool in this way, applied impaction force leads to securing of the connection between the head part 20 and the connector 40.

The assembled head component (comprising the head part 20 and the connector 40) is positioned on the spigot 14 on the stem part 12. The alignment of the head component on the stem part offset that is determined using the trial head part and the trial connector are reproduced in the head component with reference to a selected one of the markings 29 on the chamfer surface 28 which corresponds to the selected notch on the trial head part which was used previously to make a mark on the bone using the diathermy.

An impaction force is applied to the head component through an appropriate protector (such as a block of polyethylene which is configured to be a conforming fit on the bearing surface 22 of the head part 20) to cause the head component to become secured to the stem part. This is in line with existing assembly techniques for use with orthopaedic joint prostheses.

The invention claimed is:

1. An assembly for use in a procedure for implantation of an orthopaedic joint component, which comprises:
    a. a head part of the joint component having a tapered bore;
    b. a connector part that is tapered inwardly along its length such that the connector part can be received snugly in the tapered bore, the connector part having a bore having a bore axis;
    c. a tool that includes a spigot dimensioned to fit snugly into the bore of the connector part, the spigot having a spigot axis, wherein each of the tool and the connector part has a face that contact one another when the spigot is fully received in the bore of the connector part, and wherein the bore axis and the spigot axis are aligned when the spigot is received in the bore, and each of the tool and connector part faces extends generally transverse relative to the spigot axis and the bore axis; and
    d. a layer of a resilient material that covers at least part of the surface of the spigot, so that the layer of resilient material is compressed between the surface of the spigot and the internal surface of the bore in the connector part when the spigot is received in the bore.

2. The assembly of claim 1, wherein the face of the tool that contacts the connector part when the spigot is fully received in the bore is a surface that extends around the base of the spigot.

3. The assembly of claim 1, wherein the face of the connector part that contacts the tool when the spigot is fully received in the bore is a surface that extends around the bore opening.

4. The assembly of claim 1, wherein the angle between the axis of the spigot and the plane of the face on the tool is between about 75° and about 105°.

5. The assembly of claim 1, wherein the angle between the axis of the bore in the connector part and the plane of the face on the connector part is between about 75° and about 105°.

6. The assembly of claim 1, wherein the angle between the plane of the face on the connector part and the plane of the face on the tool is not more than about 15°.

7. The assembly of claim 1, wherein the bore in the connector part is inwardly tapered.

8. The assembly of claim 1, wherein the resilient material extends around the spigot in an annular arrangement.

9. The assembly of claim 8, wherein the spigot has an annular groove formed therein and wherein the resilient material is provided as an O-ring that is located partially in the groove.

10. A method of assembling an orthopaedic joint component prior to implantation, comprising the steps of:
    placing a generally annular tool having a base and a spigot that extends upwardly from the base on a generally flat surface such that the undersurface of the base is in contact with the generally flat surface;
    fitting a connector part having a bore on the spigot such that an upwardly facing surface of the tool contacts an undersurface of the connector part;
    disposing the connector part within a tapered bore of a head part; and
    applying force to the head part in a direction towards the connector part.

11. The method of claim 10, wherein the disposing step is carried out before the fitting step.

12. The method of claim 10, wherein the base has a base diameter and the head has a head diameter and the base diameter is greater than the head diameter.

13. The method of claim 10, wherein at least a part of the surface of the spigot includes a layer of a resilient material, and wherein during the applying step the layer of resilient material is compressed between the surface of the spigot and the internal surface of the bore in the connector part.

14. An assembly for use in a procedure for implantation of an orthopaedic joint component, comprising:
    a head part of the joint component having a tapered bore and a head diameter;
    a connector part that is tapered inwardly along its length such that the connector part can be received snugly in the tapered bore, the connector part having a bore having a bore axis; and
    a generally annular tool comprising a base, having a base diameter greater than the head diameter, and a spigot dimensioned to fit snugly into the bore of the connector part, the spigot having a spigot axis, wherein each of the tool and the connector part has a face that contact one another when the spigot is fully received in the bore of the connector part, and wherein the bore axis and the spigot axis are aligned when the spigot is received in the bore, and each of the tool and connector part faces extends generally transverse relative to the spigot axis and the bore axis.

15. The assembly of claim 14, further comprising a layer of resilient material that covers at least part of the surface of the spigot.

16. The assembly of claim 14, wherein the base comprises a lower surface that includes a non-slip material.

17. An assembly for use in a procedure for implantation of an orthopaedic joint component, comprising:
- a head part of the joint component having a tapered bore and a head diameter;
- a connector part that is tapered inwardly along its length such that the connector part can be received snugly in the tapered bore, the connector part having a bore having a bore axis; and
- a generally annular tool comprising a base and a spigot dimensioned to fit snugly into the bore of the connector part, the spigot having a spigot axis, wherein each of the tool and the connector part has a face that contact one another when the spigot is fully received in the bore of the connector part, wherein the bore axis and the spigot axis are aligned when the spigot is received in the bore, and each of the tool and connector part faces extends generally transverse relative to the spigot axis and the bore axis, and wherein the base comprises a lower surface that includes a non-slip material.

18. The assembly of claim 17, further comprising a layer of resilient material that covers at least part of the surface of the spigot.

19. The assembly of claim 17, wherein the base has a base diameter, and the base diameter is greater than the head diameter.

* * * * *

UNITED STATES PATENT AND TRADEMARK OFFICE
CERTIFICATE OF CORRECTION

| | | |
|---|---|---|
| PATENT NO. | : 8,128,705 B2 | Page 1 of 1 |
| APPLICATION NO. | : 12/593348 | |
| DATED | : March 6, 2012 | |
| INVENTOR(S) | : Birkbeck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this
Twenty-first Day of August, 2012

David J. Kappos
*Director of the United States Patent and Trademark Office*